(12) United States Patent
Goncz

(10) Patent No.: US 12,017,085 B1
(45) Date of Patent: Jun. 25, 2024

(54) POLARIZED LIGHT EMITTING DEVICE

(71) Applicant: Lajos Janos Goncz, Woodland Hills, CA (US)

(72) Inventor: Lajos Janos Goncz, Woodland Hills, CA (US)

( * ) Notice: Subject to any disclaimer, the term of this patent is extended or adjusted under 35 U.S.C. 154(b) by 49 days.

(21) Appl. No.: 17/964,123

(22) Filed: Oct. 12, 2022

(51) Int. Cl.
*A61N 5/06* (2006.01)
*A61N 5/00* (2006.01)
*A61N 5/073* (2006.01)

(52) U.S. Cl.
CPC .......... *A61N 5/06* (2013.01); *A61N 2005/002* (2013.01); *A61N 2005/0652* (2013.01); *A61N 2005/073* (2013.01)

(58) Field of Classification Search
CPC .............. A61N 5/06; A61N 2005/0651; A61N 2005/0652; A61N 2005/0658; A61N 2005/0659; A61N 2005/0661; A61N 2005/0663; A61N 2005/073
USPC .......................................................... 607/88
See application file for complete search history.

(56) References Cited

U.S. PATENT DOCUMENTS

| | | | | |
|---|---|---|---|---|
| 5,010,452 | A * | 4/1991 | Krebser | F21V 9/20 607/90 |
| 6,638,272 | B2 * | 10/2003 | Cho | A61B 18/203 606/8 |
| 6,875,225 | B1 * | 4/2005 | Pederson | A61M 21/00 607/90 |
| 9,458,990 | B2 * | 10/2016 | Mullani | A61B 5/0077 |
| 10,285,857 | B2 * | 5/2019 | Rubinfeld | A61F 9/013 |
| 10,722,399 | B2 * | 7/2020 | Rill | A61B 3/102 |
| 11,273,323 | B2 * | 3/2022 | Stephan | A61F 5/0118 |
| 2012/0283603 | A1 * | 11/2012 | Shapiro | A61N 7/00 601/2 |
| 2019/0142691 | A1 * | 5/2019 | Sedic | A45D 34/04 601/18 |
| 2019/0201713 | A1 * | 7/2019 | Segal | A61N 5/0617 |

* cited by examiner

*Primary Examiner* — Ahmed M Farah
(74) *Attorney, Agent, or Firm* — Edward P Dutkiewicz

(57) ABSTRACT

A device comprising an upper housing containing a polarized light emitting diode array and a plurality of electronically conductive wires coupled to the polarized light emitting diode array. The array comprises a plurality of polarized light emitting diodes capable of generating polarized light having a wavelength of one thousand, one hundred nanometers to a polarized light having a wavelength below three hundred, eighty nanometers. An intermediate arm and a lower arm rotatably couple the upper housing and a base. The base containing an electronic control module which is electronically coupled to the array of the upper housing.

9 Claims, 5 Drawing Sheets

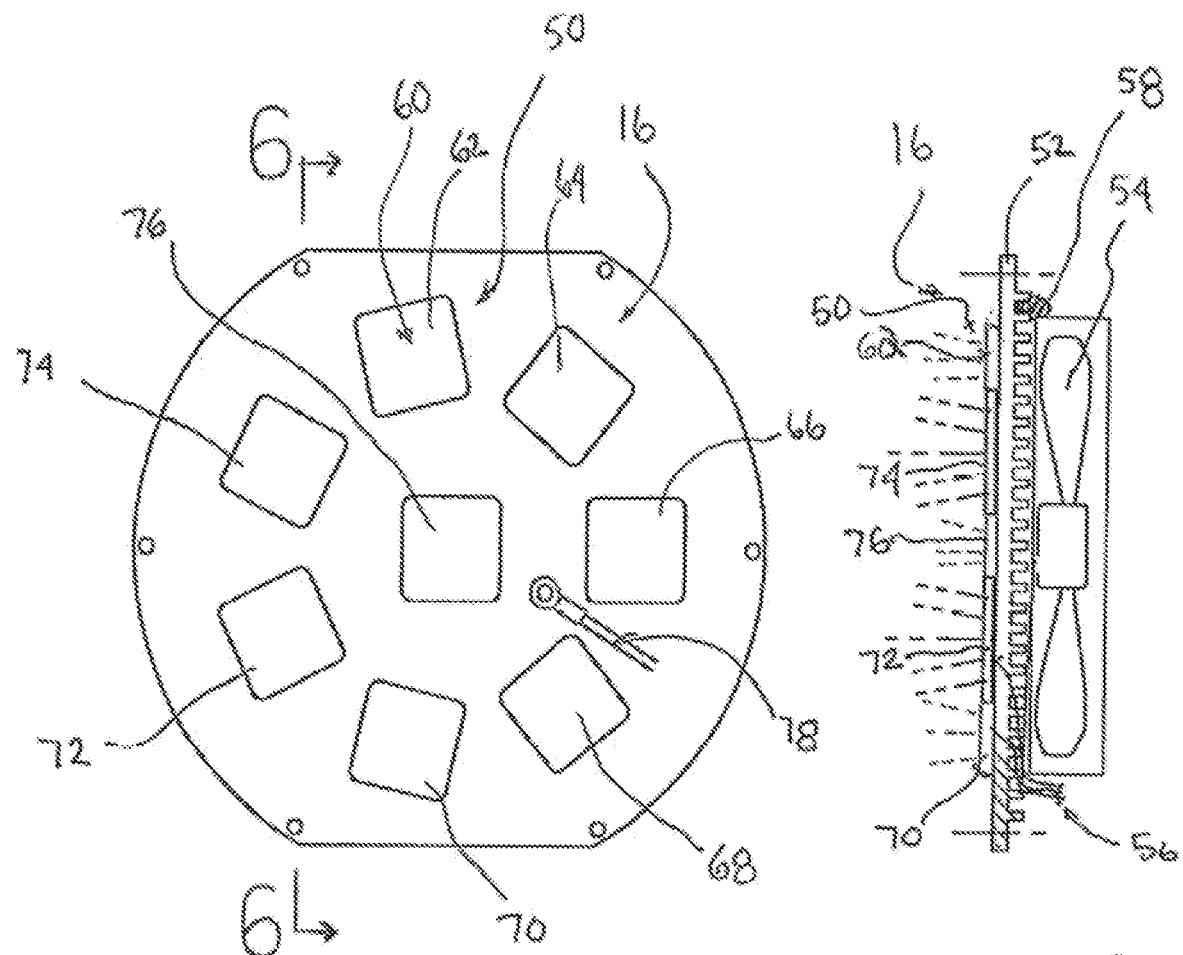

POLARIZED LIGHT EMITTING DEVICE

BACKGROUND OF THE INVENTION

Rule 1.78(F) (1) Disclosure

The Applicant has not submitted a related pending or patented non-provisional application within two months of the filing date of this present application. The invention is made by a single inventor, so there are no other inventors to be disclosed. This application is not under assignment to any other person or entity at this time.

There are no cross referenced or related applications which are direct to, or related to, the present application.

There is no research of development of this application which is federally sponsored.

FIELD OF THE INVENTION

The present invention relates to a polarized light emitting device and more particularly pertains to a device for directing polarized light, in specific wavelengths, onto a surface.

DESCRIPTION OF THE PRIOR ART

The use of light for therapy is known in the prior art. More specifically, the use of light for therapy previously devised and utilized for the purpose of providing pain relief, or healing, are known to consist basically of familiar, expected, and obvious structural configurations, notwithstanding the number of designs encompassed by the prior art which has been developed for the fulfillment of countless objectives and requirements.

While the prior art devices fulfill their respective, particular objectives and requirements, the prior art does not describe a polarized light emitting device that allows for a device to direct polarized light, in specific wavelengths, onto a surface, such as a body surface.

In this respect, the polarized light emitting device according to the present invention substantially departs from the conventional concepts and designs of the prior art, and in doing so provides an apparatus primarily developed for the purpose of a device for directing polarized light, in specific wavelengths, onto a surface.

Therefore, it can be appreciated that there exists a continuing need for a new and improved polarized light emitting device which can be used for directing polarized light, in specific wavelengths, onto a surface. In this regard, the present invention substantially fulfills this need.

SUMMARY OF THE INVENTION

In view of the foregoing disadvantages inherent in the known types of light for therapy now present in the prior art, the present invention provides an improved polarized light emitting device. As such, the general purpose of the present invention, which will be described subsequently in greater detail, is to provide a new and improved polarized light emitting device which has all the advantages of the prior art and none of the disadvantages.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another.

In describing aspects of the invention, the word "generally" may be used. The term, "generally" when used to describe a configuration means that the configuration includes those aspects which are within normal manufacturing parameters of acceptance. By way of example, the term "generally round" may be used. This should be interpreted to mean that the configuration may be perfectly round, but may also have a radius which is not exact, but is within the manufacturing parameters. For example, a basketball may be generally round, but not be perfectly round.

By adjacent to a structure is meant that the location is near the identified structure.

To attain this the goals of the Polarized Light Emitting Device, the present invention essentially comprises several components, in combination.

There is, first, an upper housing. The upper housing has a rectilinear configuration with a front surface, a rear surface, and a side surface. The side surface couples the front surface and the rear surface to form a hollow interior contained between the front surface and the rear surface. The upper housing rear surface comprises an opening, with the opening having a transparent glass layer.

The upper housing front surface has at least one heat exhaust aperture there through.

The upper housing front surface has a frontwardly displaced coupling arm. The frontwardly displaced coupling arm of the upper housing front surface has an upper surface, a lower surface, and a pair of side surfaces. The frontwardly displaced coupling arm of the upper housing rear surface has a rounded proximal terminus and a flat distal terminus. The pair of side surfaces of the frontwardly displaced coupling arm each have a proximal pivot aperture there through. The proximal pivot aperture of the frontwardly displaced coupling arm has an associated first pivot pin.

The upper housing side surface has a wire hole there through, with the wire hole having an associated coupling wire passing through the wire hole.

The upper housing hollow interior contains a polarized light emitting diode array, a heat sink, an electric motor driven fan, and a plurality of electronically conductive wires coupled to the polarized light emitting diode array, a ground wire, and an electric motor which drives the fan. The electronically conductive wires of the upper housing hollow interior are operatively and electronically coupled to the upper housing side surface coupling wire. The coupling wire passes through the wire hole in the upper housing side surface. The upper housing heat sink has an associated heat sensor coupled there to.

The polarized light emitting diode array comprises a plurality of polarized light emitting diodes one of which is an infrared light emitting diode which generates a polarized light in the wavelength range of seven hundred, sixty nanometers to one thousand, one hundred nanometers. There is also a red light emitting diode which generates a polarized light in the wavelength range of six hundred, ten nanometers to seven hundred, sixty nanometers and an orange light emitting diode which generates a polarized light in the wavelength range of five hundred, seventy nanometers to five hundred, ninety nanometers. The array also includes a yellow light emitting diode which generates a polarized light in the wavelength range of five hundred, seventy nanometers to five hundred, ninety nanometers and a green light emitting diode which generates a polarized light in the wavelength range of five hundred, fifty nanometers to five hundred, seventy nanometers. There is also a blue light emitting diode which generates a polarized light in the wavelength range of four hundred, fifty nanometers to five hundred nanometers and a purple light emitting diode which generates a polarized light in the wavelength range of three hundred, eighty nanometers to four hundred, fifty nanometers. Lastly, there is an ultra violet light emitting diode which generates a polarized light in the wavelength below three hundred, eighty nanometers.

There is an intermediate arm which is coupled to the upper housing. The intermediate arm has an upper surface, a lower surface, and a pair of side surfaces. The intermediate arm has a distal terminus and a proximal terminus. The pair of side surfaces each have a distal pivot pin aperture and a proximal pivot pin aperture there through. The distal pivot pin aperture is rotatably coupled to the proximal pivot aperture of the frontwardly displaced coupling arm by the associated first pivot pin.

There is a lower arm which is coupled to the intermediate arm. The lower arm has a distal end. The lower arm distal end has a distal pivot aperture there through. The lower arm distal end pivot aperture has an associated second pivot pin. The associated second pivot pin rotatably couples the proximal pivot pin aperture of the intermediate arm and the lower arm distal end pivot aperture. The lower arm has a proximal end, with the proximal end of the lower arm having a rotatable downwardly extending shaft.

There is a base. The base has a flat lower surface with a plurality of rubber feet. The base has a front surface with the front surface having a power cord aperture there through, with an associated power cord. The base has a rear surface. The rear surface has a coupling wire aperture there through for allowing the coupling wire to electronically couple the base and the upper housing The base has a pair of side surfaces being a right side surface and a left side surface. The base right side surface having an on/off switch aperture, with the on/off switch aperture having an associated on/of switch. The base has an upper surface forming an upward projection. The upper surface of the base has a touch screen aperture there through with the touch screen aperture having an associated touch screen. The upper surface of the base has a extending shaft recess therein. The extending shaft recess is configured to mate with and receive the rotatable downwardly extending shaft of the lower arm. The base upper surface and base lower surface and base side surfaces form a base hollow interior.

There is an electronic control module. The electronic control module is disposed within the hollow interior of the base. The electronic control module comprises a plate. The plate is coupled to the base lower surface with a plurality of fasteners. The plate has a ground wire which is coupled to a plate ground. The ground wire runs from the base plate to the upper housing array, and grounds to two components to each other, and to ground. The electronic control module has an associated electronic coupler, cooling fan, controller processor, twelve volt power supply, and twenty four volt power supply. The electronic control module has a buss which couples the electronic coupler to the controller processor, twelve volt power supply, and twenty four volt power supply. The buss also electronically couples the coupling wire which runs from the base to the upper housing. The upper housing heat sink sensor is electronically coupled to the electronic control module.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved polarized light emitting device which has all of the advantages of the prior art light for therapy and none of the disadvantages.

It is another object of the present invention to provide a new and improved polarized light emitting device which may be easily and efficiently manufactured and marketed.

It is further object of the present invention to provide a new and improved polarized light emitting device which is of durable and reliable constructions.

An even further object of the present invention is to provide a new and improved polarized light emitting device which is susceptible of a low cost of manufacture with regard to both materials and labor, and which accordingly is then susceptible of low prices of sale to the consuming public, thereby making such polarized light emitting device economically available to the buying public.

Even still another object of the present invention is to provide a polarized light emitting device for directing polarized light, in specific wavelengths, onto a surface.

Lastly, it is an object of the present invention to provide a new and improved polarized light emitting device, comprising several components, in combination, being an upper housing containing a polarized light emitting diode array and a plurality of electronically conductive wires coupled to the polarized light emitting diode array. The polarized light array having a plurality of polarized light emitting diodes which generate distinct wavelengths of colored light between wavelength of three hundred, eighty and the wavelength of one thousand, one hundred. A base is coupled to the upper housing. The base contains an electronic control module and two voltage power supplies, being a twelve volt power supply and twenty four volt power supply. the electronic control module having a buss which couples the electronic coupler to the controller processor and twelve volt power supply and twenty four volt power supply, the buss also being electronically coupled to a coupling wire which runs from the base to the array located in the upper housing.

It should be understood that while the above-stated objects are goals which are sought to be achieved, such objects should not be construed as limiting or diminishing the scope of the claims herein made.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is close up view of the light emitting diode array.

FIG. 6 is a cross sectional view of line 6-6 of FIG. 5.

The same reference numerals refer to the same parts throughout the various Figures.

DESCRIPTION OF THE PREFERRED EMBODIMENT

Figure 1:
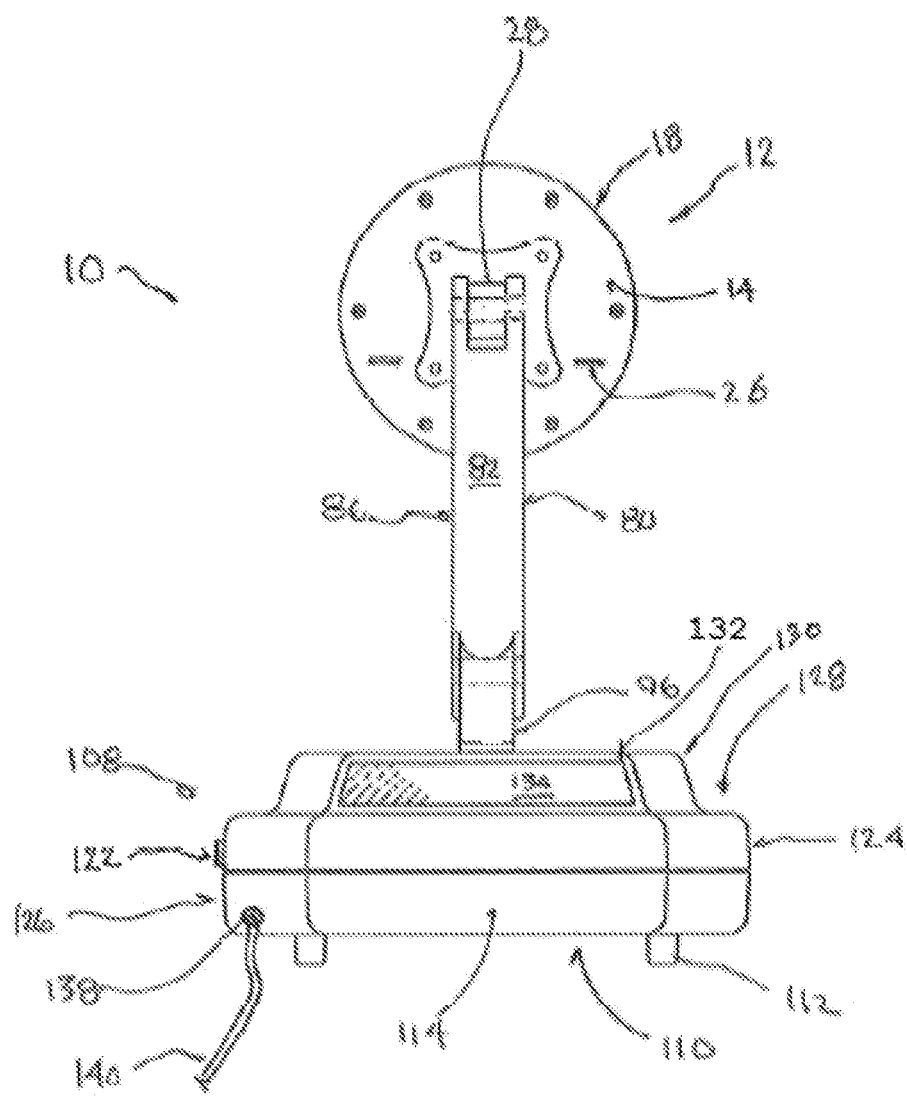
FIG. 1 is a front elevational view of the polarized light emitting device.
Figure 2:
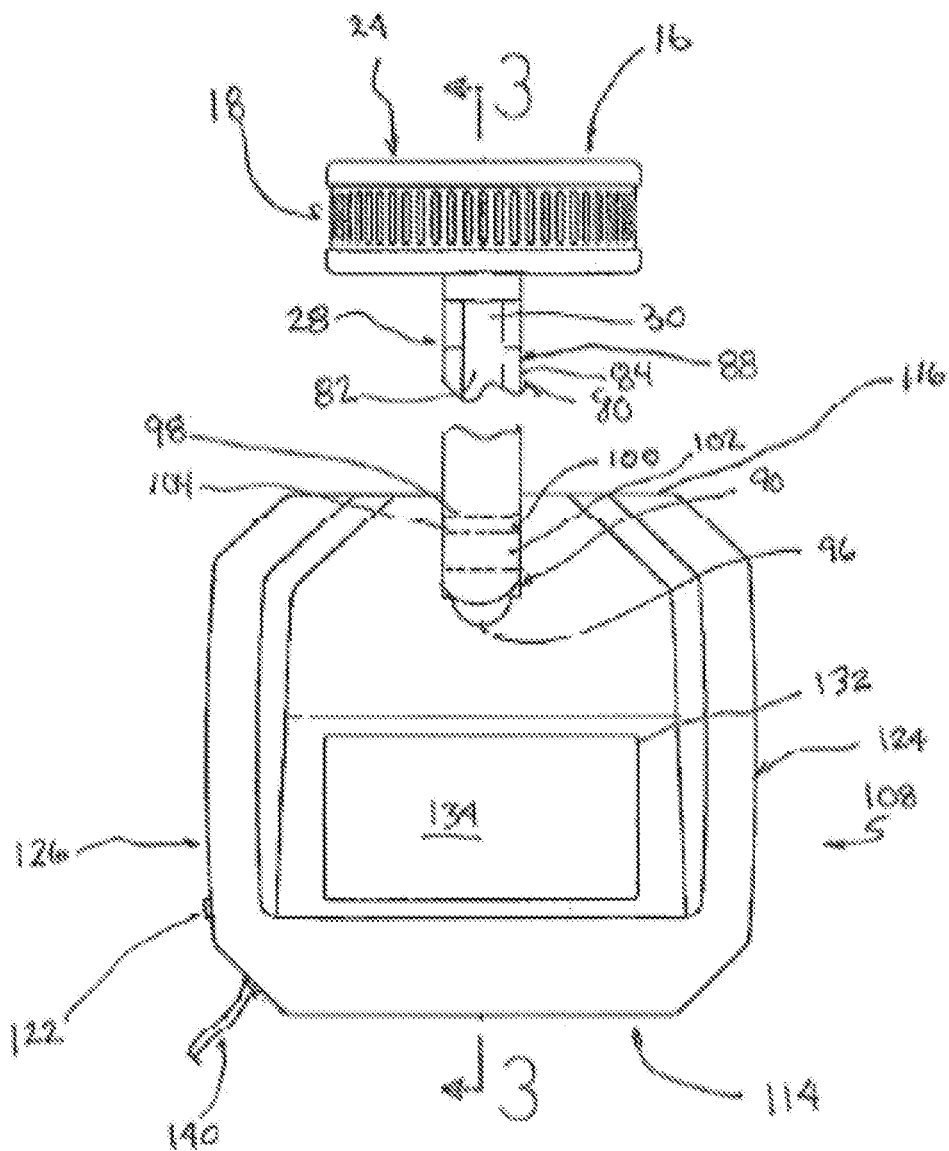
FIG. 2 is atop plan view of the polarized light emitting device.
Figure 3:
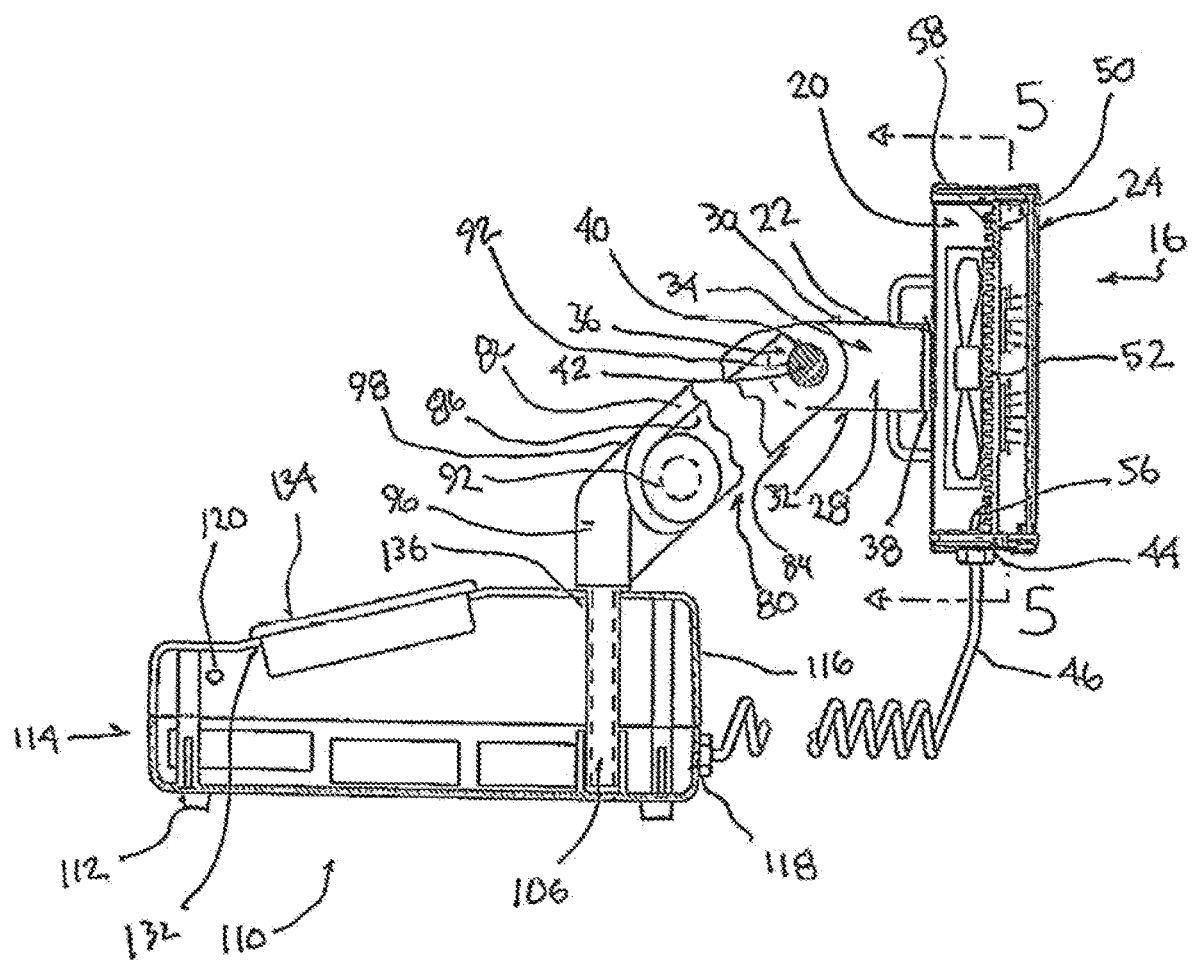
FIG. 3 is a cross sectional view of the polarized light emitting device taken along line 3-3 of FIG. 2.
Figure 4:
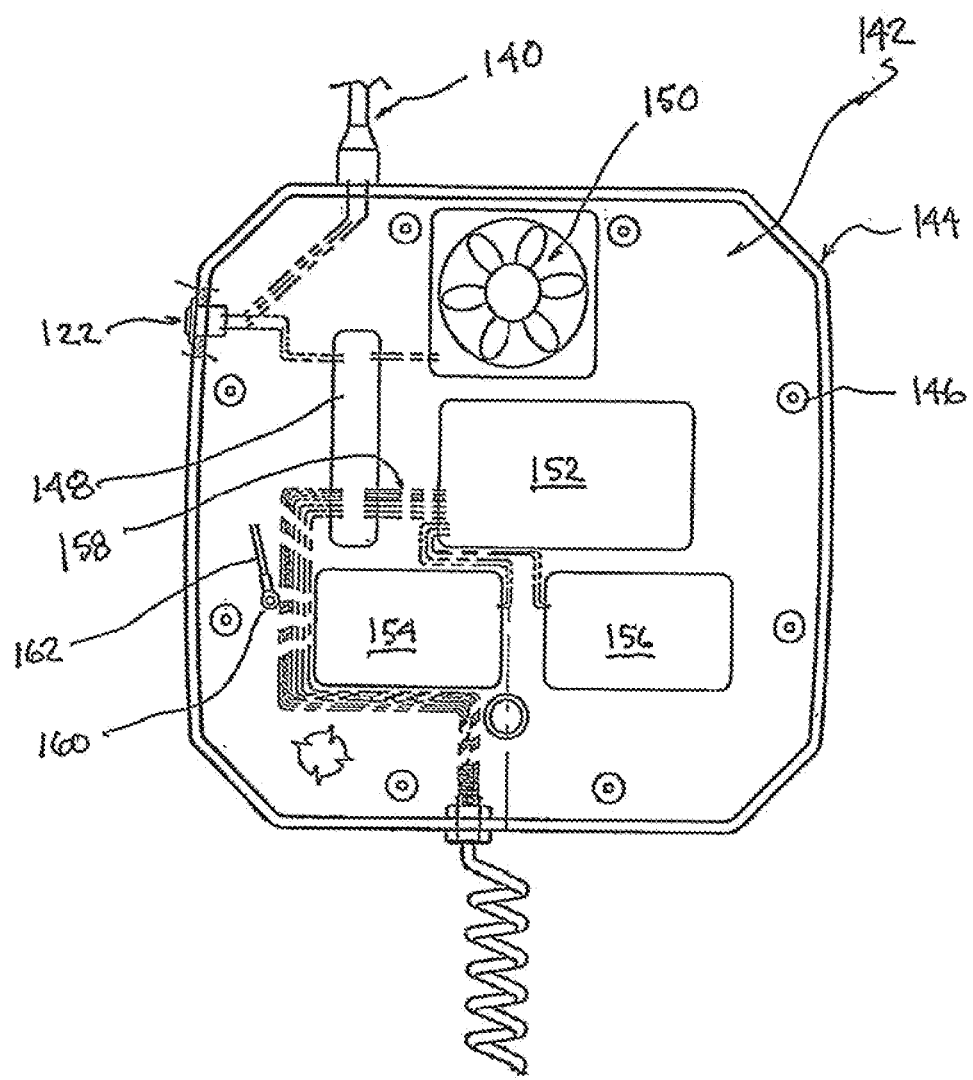
FIG. 4 is a cross sectional view of the polarized light emitting device electronic control module taken along line 4-4 of FIG. 3.

With reference now to the drawings, and in particular to FIG. 1 thereof, the preferred embodiment of the new and improved polarized light emitting device, embodying the principles and concepts of the present invention and generally designated by the reference numeral 10, will be described.

The present invention, the polarized light emitting device 10 is comprised of a plurality of components. Such components in their broadest context include an upper housing containing a light emitting diode array, a set of coupling arms, a base, and an electronic control module housed within the base. Such components are individually configured and correlated with respect to each other so as to attain the desired objective.

A polarized light emitting device 10, comprises several components, in combination.

There is, first, an upper housing 12. The upper housing has a rounded configuration with a front surface 14, a rear surface 16, and a circumferential side surface 18. The circumferential side surface couples the front surface and the rear surface to form a hollow interior 20 contained between the front surface and the rear surface. The upper housing rear surface comprises an opening 22, with the upper housing rear surface opening having a transparent glass layer 24.

The upper housing front surface has at least one heat exhaust aperture 26 there through.

The upper housing rear surface has a frontwardly displaced coupling arm 28. The frontwardly displaced coupling arm of the upper housing rear surface has an upper surface 30, a lower surface 32, and a pair of side surfaces 34. The frontwardly displaced coupling arm of the upper housing rear surface has a proximal rounded terminus 36 and a flat distal terminus 38. The pair of side surfaces of the frontwardly displaced coupling arm each have a proximal pivot aperture 40 there through. The proximal pivot aperture of the frontwardly displaced coupling arm has an associated first pivot pin 42.

The upper housing circumferential side surface has a wire hole 44 there through, with the wire hole having an associated coupling wire 46 passing through the upper housing circumferential side surface wire hole.

The upper housing hollow interior contains a polarized light emitting diode array 50, a heat sink 52, an electric motor driven fan 54, and a plurality of electronically conductive wires 56 coupled to the polarized light emitting diode array, and the electric motor of the fan. The electronically conductive wires of the upper housing hollow interior are operatively and electronically coupled to the upper housing side surface coupling wire. The coupling wire passes through the wire hole in the upper housing side surface. The upper housing heat sink has an associated heat sensor 58 coupled there to.

The polarized light emitting diode array comprises a plurality of polarized light emitting diodes 60 being an infrared light emitting diode 62 which generates a polarized light in the wavelength range of seven hundred, sixty nanometers to one thousand, one hundred nanometers. There is also a red light emitting diode 64 which generates a polarized light in the wavelength range of six hundred, ten nanometers to seven hundred, sixty nanometers and an orange light emitting diode 66 which generates a polarized light in the wavelength range of five hundred, seventy nanometers to five hundred, ninety nanometers. The array also includes and a yellow light emitting diode 68 which generates a polarized light in the wavelength range of five hundred, seventy nanometers to five hundred, ninety nanometers and a green light emitting diode 70 which generates a polarized light in the wavelength range of five hundred, fifty nanometers to five hundred, seventy nanometers. There is also a blue light emitting diode 72 which generates a polarized light in the wavelength range of four hundred, fifty nanometers to five hundred nanometers and a purple light emitting diode 74 which generates a polarized light in the wavelength range of three hundred, eighty nanometers to four hundred, fifty nanometers. Lastly, there is an ultra violet light emitting diode 76 which generates a polarized light in the wavelength below three hundred, eighty nanometers. The polarized light emitting diode array has a coupling ground wire 78.

There is an intermediate arm 80 which is coupled to the upper housing. The intermediate arm has an upper surface 82, a lower surface 84, and a pair of side surfaces 86. The intermediate arm has a distal terminus 88 and a proximal terminus 90. The pair of side surfaces each have a distal pivot pin aperture 92 and a proximal pivot pin aperture 94 there through. The distal pivot pin aperture is rotatably coupled to the proximal pivot aperture of the frontwardly displaced coupling arm by the associated first pivot pin 42.

There is a lower arm 96 which is coupled to the intermediate arm. The lower arm has a distal end 98. The lower arm distal end has a distal pivot aperture 100 there through. The lower arm distal end pivot aperture has an associated second pivot pin 102. The associated second pivot pin rotatably couples the proximal pivot pin aperture of the intermediate arm 104 and the lower arm distal end pivot pin aperture. The lower arm has a proximal end, with the proximal end having a rotatable downwardly extending shaft 106.

There is a base 108. The base has a flat lower surface 110 with a plurality of rubber feet 112. The base has a front surface 114 with a power cord aperture there through 138, with an associated power cord 140. The base has a rear surface 116, with the rear surface having a coupling wire aperture there through 118, with the associated coupling wire 46. The base also has an on/off switch aperture 120, with the on/off switch aperture having an associated on/of switch 122.

The base has a pair of side surfaces being a right side surface 124 and a left side surface 126. The base has an upper surface 128 forming an upward projection 130. The upper surface of the base has a touch screen aperture 132 there through with the touch screen aperture having an associated touch screen 134. The upper surface of the base has a extending shaft recess therein 136. The extending shaft recess is configured to mate with and receive the rotatable downwardly extending shaft of the lower arm. The base upper surface and lower surface and side surfaces form a hollow interior of the base. The base has power cord aperture 138 an associated power cord 140.

There is an electronic control module 142. The electronic control module is disposed within the hollow interior of the base. The electronic control module has a plate 144. The plate is coupled to the base lower wall with a plurality of fasteners 146.

The electronic control module has an associated electronic coupler 148, cooling fan 150, controller processor 152, twelve volt power supply 154, and twenty four volt power supply 156. The electronic control module has a buss 158 which couples the electronic coupler to the controller processor, twelve volt power supply, and twenty four volt power supply. The buss also electronically couples the coupling wire which runs from the base to the upper housing. The plate has a ground area 160 with an attached ground wire 162. The Electronic Control Module is electronically coupled to the power wire 140 and an on/of switch 122.

The present invention relates to the field of medical device, that provides polarized light emitting device which generates a polarized beam by LED (Light Emitting Diode) from 200 to 1100 nanometers in a constant or pulsed beaming mode. It is known that light energy has impacts on tissues, bones, organs, bacterias, viruses, cells, cancer cells, as well as on blood cancers, pancreas tumors and pancreas dysfunction, liver tumors and liver diseases, heart muscle, producing oxygenated red blood cells, joint disease, rheumatic arthritis, and viruses. Exposing the affected body to the beaming of the polarized light emitting device may have an influence on the above-described cells and organs.

The polarized light emitting device is comprised of (8) eight colors which vary in light wavelength from 200 nanometer in wavelength to 1100 nanometers in wavelength. The various wavelength have different impacts on the tissues, cells, organs, muscles and reproduction of the Red Blood cells.

The polarized light emitting device generator wavelengths are, in nanometers (nm):
Ultra Violet below 380 nm; Purple 380 nm to 450 nm, Green 550 nm to 570 nm; Orange 570 nm to 590 nm; Red 610 nm to 760 nm and Infra-Red 760 nm to 1,100 nm.

The polarized light emitting device, light generator, which is referred to as the polarized light emitting diode array, is located in the upper housing.

The system is governed by a microprocessor, referred to, herein, as the controller processor. The controller processor is programmable through the touch screen which is coupled to the base.

In use, a user selects the wavelength of light the user wishes the array to produce. The user also programs the mode of the beaming, whether it is constant or pulsed beaming. The user then selects the length of the treatment cycle, which is selectable from one to twenty minutes. The duration of the light treatment is limited and will not exceed twenty minutes. The upper housing has a heat sink which has a temperature sensor coupled thereto. The temperature sensor monitors temperature of the upper housing interior as well as the temperature of the heat sink and diode array. The temperature sensor communicates electronically with the controller processor and the controller processor and will shut the unit down if the temperature of the upper housing exceeds a predetermined temperature.

The system operates in a voltage range of one hundred and ten volts to two hundred and twenty volts, alternating current. The electronic system has two power sources, one being a twelve volt source and the other being a twenty four volt source. In generating specific wavelengths of light, it may be necessary to use either twelve volt source, a twenty four volt, or the system may require a combination of the twelve volt and twenty four volt sources, to provide a thirty six volt power source. The program contains a timer which limits the time the light treatment is administered. When the time limit is reached, a buzzer sounds, indicating that the time limit has been reached, and the cycle is complete. The system is then shut down, and the treatment parameters are reset in the controller processor to zero. The system may then be activated to provide another treatment cycle, with the user then entering in new parameters, such as wavelength, pulsed or constant mode, and time.

In use, the polarized light emitting device operates in the following manner. The device is a stand alone, meaning the base rests on a surface and the upper housing is disposed in the direction of a desire treatment. The arm which couples the base to the upper housing allows a user to adjust the location and direction of the light beam toward that location which the user wishes to treat.

The artificial polarized light which is generated by the polarized light emitting device does not contain any harmful ultra violet light, which is known to be a potential source of, or causative agent of, "skin cancer". The device herein described, provides an increased quantity of color energy and penetration deep into the body for ultimate results. Here the light is the medium, which transports energy deep into a user's body to reach the blood circulation and organs for beneficial reaction.

Other advantages of using specific wavelengths of light include the following:
1) WOUND STERILIZATION: Polarized Color Light Energy (PCLE) have fatal impacts on Bacteria for sterilization of open wounds. Other effect have that speeds up the healing process; 2) TREATMENT OF DIABETES: The Pancreas Cells produces insulin for the body needs. For unknown reason the cells are stop producing insulin. The PCLE may rejuvenate the cells and start the production of insulin, to re-establish the body's insulin balance; 3) RHEUMATOID ARTHRITIS (RA): Inflammations of the joints mostly in older folks becomes swelling and painful, the PCLE smothers the affected area and help to regenerate the cart ledges; 4) COIN FORMED RED BLOOD CELLS SEPARATION (ROULEAUX FORMATION): Due to old age or sickness the blood pH may become acidic and the red blood cells stick together in a coin formation, which prevented the uptake and transport of oxygen. With time, this condition becomes more severe, and may lead to forming a blood clot, which may contribute to a heart attack, and or an aneurism. The blood exposed to PCLE may separate from the coin formation and the red blood cells may then oxygenate the tissue. Such an increase in oxygenation may increase function of the immune system; 5) MELANOMA MULTIPLEX (Blood Cancer). Blood Cancer, when it is diagnosed, is usually fatal, in 1-2 years. Light Chains refer to both Kappa and lambda light chains, which like together with other proteins (heavy chains) to form immunoglobulins, also known as antibodies, which target and neutralize bacteria and viruses. In disease states, when the serum Lambda light chain level increases to over 110, the disease process becomes fatal. Using specific light wave length therapy, it is believed that the serum levels of light chains was reduced. Such a reduction is thought to increase life expectancy, in the presence of disease; 6) TREATING OPEN WOUNDS: In open wounds, bacteria can multiply very rapidly, even if the wound is cleansed with disinfectant liquid. The Polarized Color Light Energy (PCLE) may have antibacterial property, and may be beneficial to the healing process; 7) BREAST CANCER THERAPY: It is believed that Breast Cancer cells may be destroyed if the breast cancer cells are exposed to specific wavelengths of light. It is believed that the light works to destroy cancer cell membranes, thereby destroying the cancer cells. The exposure can be achieved through the skin, as the specific light wavelengths may penetrate the skin, deep into the tissues; 8) JAUNDICE: It is believed that jaundice is decreased when the body surface is exposed to "Blue" light; 9) NORTHERN BLUES: During wintertime the limitation of light reaching the skin surface may contribute to a decrease in Vitamin D, and a person become depressed and moody. It is believed that expose to specific wavelengths of light will increase vitamin D production, thereby relieving the depression and moodiness a person may experience; (10) BRAIN STIMULATION: It is believed that specific wavelengths of light may enhance brain function.

Specific wavelengths of light may also be beneficial in agriculture. IL is well known that plants utilize light to produce energy (photosynthesis). It is believed that specific light wavelengths may be used to eradicate or control harmful pathogens, funguses and other parasites in the field of grapes, fruits, vegetables, potatoes, and bell peppers. The use of specific wavelengths of light to control field pests would eliminate the use of toxic chemicals, which are currently used to achieve the same pest control.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A polarized light emitting device, comprising several components, in combination, being:
    an upper housing having a rectilinear configuration with an front surface and a rear surface and a side surface, with the side surface connecting the front surface and the rear surface to form a hollow interior contained between the front surface and the rear surface;
    the upper housing rear surface comprising an opening;
    the upper housing front surface having a frontwardly displaced coupling arm;
    the upper housing hollow interior containing a polarized light emitting diode array and a plurality of electronically conductive wires coupled to the polarized light emitting diode array;
    the polarized light emitting diode array comprising a plurality of polarized light emitting diodes being an infrared light emitting diode which generates a polarized light in the wavelength range of seven hundred, sixty nanometers to one thousand, one hundred nanometers and a red light emitting diode which generates a polarized light in the wavelength range of six hundred, ten nanometers to seven hundred, sixty nanometers and an orange light emitting diode which generates a polarized light in the wavelength range of five hundred, seventy nanometers to five hundred, ninety nanometers and a yellow light emitting diode which generates a polarized light in the wavelength range of five hundred, seventy nanometers to five hundred, ninety nanometers and a green light emitting diode which generates a polarized light in the wavelength range of five hundred, fifty nanometers to five hundred, seventy nanometers and a blue light emitting diode which generates a polarized light in the wavelength range of four hundred, fifty nanometers to five hundred nanometers and a purple light emitting diode which generates a polarized light in the wavelength range of three hundred, eighty nanometers to four hundred, fifty nanometers and an ultra violet light emitting diode which generates a polarized light in the wavelength below three hundred, eighty nanometers;
    an intermediate arm coupled to the frontwardly displaced coupling arm of the upper housing front surface;
    a lower arm having a distal end, the lower arm being operatively coupled to the intermediate arm;
    a base coupled to the lower arm, the base having a front surface and a rear surface, the front surface of the base having a power cord aperture there through, the base having a pair of side surfaces being a right side surface and a left side surface, the base upper surface and lower surface and side surfaces forming a hollow interior; and
    an electronic control module being disposed within the hollow interior of the base, the electronic control module having an associated electronic coupler and cooling fan and controller processor and twelve volt power supply and twenty four volt power supply, the electronic control module having a buss which couples the electronic coupler to the controller processor and twelve volt power supply and twenty four volt power supply, the buss also being electronically coupled to a coupling wire which runs from the base to the upper housing, the electronic control module being electronically coupled to the upper housing array by a coupling wire.

2. The polarized light emitting device as described in claim 1, with the polarized light emitting device further comprising:

the frontwardly displaced coupling arm of the upper housing front surface having an upper surface and a lower surface and a pair of side surfaces;

the upper housing hollow interior containing a heat sink;

the electronically conductive wires of the upper housing hollow interior being operatively and electronically coupled to the coupling wire;

the intermediate arm having an upper surface and a lower surface and a pair of side surfaces;

the base upper surface having a touch screen aperture there through with the touch screen aperture having an associated touch screen; and the electronic control module comprising a plate.

3. The polarized light emitting device as described in claim 2, with the polarized light emitting device further comprising:

the upper housing front surface opening having a transparent glass layer covering the light emitting diode array;

the upper housing hollow interior containing an electric motor driven fan;

the intermediate arm having a distal terminus and a proximal terminus;

the lower arm distal end having a distal pivot aperture there through; and the upper housing side surface having a coupling wire hole there through.

4. The polarized light emitting device as described in claim 3, with the polarized light emitting device further comprising:

the upper housing side surface coupling wire hole having the coupling wire passing through the wire hole;

the intermediate arm side surfaces each having a distal pivot pin aperture and a proximal pivot pin aperture there through;

the lower arm distal end pivot aperture having an associated second pivot pin, the associated second pivot pin rotatably coupling the proximal pivot pin aperture of the intermediate arm and the lower arm distal end pivot pin aperture;

the base having a flat lower surface;

the base front surface having a power cord aperture there through with an associated power cord;

the base upper surface forming an upward projection;

the base upper surface having a extending shaft recess therein;

the coupling wire passes through the upper housing side surface wire hole which passes through the upper housing side surface; and the electronic control module plate having a ground wire which is coupled to a plate ground.

5. The polarized light emitting device as described in claim 4, with the polarized light emitting device further comprising:

the upper housing front surface having at least one heat exhaust aperture there through;

the frontwardly displaced coupling arm of the upper housing rear surface having a proximal rounded terminus and a flat distal terminus;

the lower arm having a proximal end with the proximal end having a rotatable downwardly extending shaft;

the base flat lower surface having a plurality of rubber feet;

the base extending shaft recess being configured to mate with and receive the rotatable downwardly extending shaft of the lower arm;

the upper housing heat sink having an associated heat sensor coupled there to; and the electronic control module plate being coupled to the base lower wall with a plurality of fasteners.

6. The polarized light emitting device as described in claim 5, with the polarized light emitting device further comprising:

the pair of side surfaces of the frontwardly displaced coupling arm having a proximal pivot aperture there through; and the base having an on/of switch hole there through with an associated on/of switch electronically coupled to the control module.

7. The polarized light emitting device as described in claim 6, with the polarized light emitting device further comprising:

the proximal pivot aperture of the rearwardly displaced coupling arm having an associated first pivot pin; and the intermediate arm distal pivot pin aperture being rotatably coupled to the proximal pivot aperture of the frontwardly displaced coupling arm by the associated first pivot pin.

8. A polarized light emitting device, comprising several components, in combination, being:

an upper housing containing a polarized light emitting diode array and a plurality of electronically conductive wires coupled to the polarized light emitting diode array;

the polarized light emitting diode array comprising a plurality of polarized light emitting diodes capable of generating polarized light having a wavelength of one thousand, one hundred nanometers to a polarized light having a wavelength below three hundred, eighty nanometers;

an intermediate arm and a lower arm rotatably coupling the upper housing and a base; and the base coupled to the lower arm, the base containing an electronic control module, the electronic control module being electronically coupled to the array by a coupling wire which electronically couples the electronic control module to the array of the upper housing.

9. The polarized light emitting device as described in claim 8, with the polarized light emitting device further comprising the electronic control module having a twelve volt power source and a twenty four volt power source.

* * * * *